(12) United States Patent
Versalovic et al.

(10) Patent No.: US 12,201,656 B2
(45) Date of Patent: *Jan. 21, 2025

(54) SELECTION OF BACTERIAL STRAINS USEFUL IN ALLERGY TREATMENT

(71) Applicant: BioGaia AB, Stockholm (SE)

(72) Inventors: James Versalovic, Bellaire, TX (US); Bo Mollstam, Lerum (SE); Bhanu Priya Ganesh, Houston, TX (US)

(73) Assignee: BioGaia AB, Stockholm (SE)

( * ) Notice: Subject to any disclaimer, the term of this patent is extended or adjusted under 35 U.S.C. 154(b) by 641 days.

This patent is subject to a terminal disclaimer.

(21) Appl. No.: 17/462,227

(22) Filed: Aug. 31, 2021

(65) Prior Publication Data

US 2022/0008491 A1    Jan. 13, 2022

Related U.S. Application Data

(63) Continuation of application No. 16/099,258, filed as application No. PCT/SE2017/050455 on May 8, 2017, now Pat. No. 11,135,255.

(30) Foreign Application Priority Data

May 9, 2016   (SE) .................................. 1650620-6

(51) Int. Cl.
| | | |
|---|---|---|
| A61K 35/747 | (2015.01) | |
| A61K 35/741 | (2015.01) | |
| A61K 35/744 | (2015.01) | |
| A61K 45/06 | (2006.01) | |
| A61P 37/08 | (2006.01) | |
| C12Q 1/6876 | (2018.01) | |

(52) U.S. Cl.
CPC .......... *A61K 35/747* (2013.01); *A61K 35/741* (2013.01); *A61K 35/744* (2013.01); *A61K 45/06* (2013.01); *A61P 37/08* (2018.01); *C12Q 1/6876* (2013.01); *C12Q 2600/158* (2013.01)

(58) Field of Classification Search
CPC .. A61K 35/747; A61K 35/741; A61K 35/744; A61K 45/06; A61P 37/08; C12Q 1/6876; C12Q 2600/158
See application file for complete search history.

(56) References Cited

U.S. PATENT DOCUMENTS

| | | |
|---|---|---|
| 4,525,358 A | 6/1985 | Baltes et al. |
| 8,003,092 B2 | 8/2011 | Yamamoto et al. |
| 2013/0022586 A1 | 1/2013 | Versalovic et al. |
| 2018/0104287 A1 | 4/2018 | Versalovic et al. |

FOREIGN PATENT DOCUMENTS

| | | | |
|---|---|---|---|
| KR | 1020040068820 | 8/2004 | |
| WO | WO-2004022727 A1 * | 3/2004 | ........... A23L 33/135 |

OTHER PUBLICATIONS

Aaronson DW. Evaluation of cetirizine in patients with allergic rhinitis and perennial asthma. Ann Allergy Asthma Immunol. May 1996;76(5):440-6. doi: 10.1016/S1081-1206(10)63461-8. PMID: 8630718., Abstract Only. (Year: 1996).*
Ouwehand AC, Nermes M, Collado MC, Rautonen N, Salminen S, Isolauri E. Specific probiotics alleviate allergic rhinitis during the birch pollen season. World J Gastroenterol. Jul. 14, 2009;15(26):3261-8. doi: 10.3748/wjg.15.3261. PMID: 19598302; PMCID: PMC2710782. (Year: 2009).*
Jerga A, Lu YJ, Schujman GE, de Mendoza D, Rock CO. Identification of a soluble diacylglycerol kinase required for lipoteichoic acid production in Bacillus subtilis. J Biol Chem. Jul. 27, 2007;282(30):21738-45. doi: 10.1074/jbc.M703536200. Epub May 28, 2007. PMID: 17535816. (Year: 2007).*
Excerpt from https://medlineplus.gov/druginfo/meds/a698026.html Accessed Sep. 10, 2020.
Gen Bank EGC 15283.1 for dag K.
"International Search Report and Written Opinion, PCT/SE2017/050455, mailed Jul. 12, 2017, 9 pp."
Ganesh BP , et al., "hdcA+L. reuteri 6475 inhibits H1R downstream signaling via dagK and causes immunosuppression of intestinal epithelium in gnotobiotic mice. The FASEB Journal. Apr. 2016; 30(1) Supplement 1018.1, 2 pp."
Wang Y , et al., "DGKalpha DNA vaccine relieves airway allergic inflammation in asthma model possibly via induction of T-cell anergy.Int J Clin Exp Pathol. Jan. 2013; 6(11): 2404-2411."

* cited by examiner

*Primary Examiner* — Kade Ariani
(74) *Attorney, Agent, or Firm* — Myers Bigel, P.A.

(57) ABSTRACT

Bacterial strains useful in prophylaxis, inhibition and/or treatment of an allergy in a mammal are selected by screening bacterial strains for capability of producing diacylglycerol kinase (DagK). A bacterial strain which is capable of producing DagK is then selected for use in prophylaxis, inhibition and/or treatment of the allergy.

7 Claims, 4 Drawing Sheets

Specification includes a Sequence Listing.

SELECTION OF BACTERIAL STRAINS USEFUL IN ALLERGY TREATMENT

STATEMENT REGARDING ELECTRONIC FILING OF A SEQUENCE LISTING

A Sequence Listing in ASCII text format, submitted under 37 C.F.R. § 1.821, entitled 9737-69CT_ST25.txt, 4086 bytes in size, generated on Sep. 25, 2021 and filed via EFS-Web, is provided in lieu of a paper copy. This Sequence Listing is incorporated by reference into the specification for its disclosures.

STATEMENT OF PRIORITY

This application is a continuation application of U.S. patent application Ser. No. 16/099,258, filed on Nov. 6, 2018, which is a 35 U.S.C. § 371 national phase entry of International Application Serial No. PCT/SE2017/050455, filed May 8, 2017, and which claims the benefit, under 35 U.S.C. § 119 (a), of Swedish Patent Application No. 1650620-6, filed May 9, 2016, the disclosure of each of which is incorporated herein by reference in its entirety.

TECHNICAL FIELD

The present embodiments generally relate to selection of bacterial strains, and in particular to selection of bacterial strains useful in prophylaxis, inhibition and/or treatment of allergy, and uses thereof.

BACKGROUND

Allergies, also known as allergic reactions or diseases, are a number of conditions caused by hypersensitivity of the immune system to something in the environment. Allergies include, for instance, allergic rhinitis, also referred to as hay fever; food allergies; atopic dermatitis, also referred to as atopic eczema; allergic asthma; and anaphylaxis. Symptoms generally vary depending on the type of allergy. For instance, food allergy, which is an abnormal immune response to food, may cause signs and symptoms that range from mild to severe itchiness, swelling of the tongue, vomiting, diarrhoea, hives, trouble breathing, or low blood pressure. This typically occurs within minutes to several hours of exposure. When the symptoms are severe it is known as anaphylaxis.

Common allergens, i.e., antigens that produce an abnormally vigorous immune response in which the immune system fights off a perceived threat that would otherwise be harmless to the body, include, among others, pollen and food. The underlying mechanism involves immunoglobulin E antibodies (IgE) binding to an allergen and then to a receptor on mast cells or basophils where it triggers the release of inflammatory chemicals, such as histamine.

Current treatments for allergies include avoiding known allergens and the use of medications, such as antihistamines. An antihistamine is a medicament that opposes the activity of histamine receptors in the body. Antihistamines are subclassified according to the histamine receptor that they act upon. The two largest classes of antihistamines are H1-antihistamines and H2-antihistamines. Antihistamines that target the histamine H1-receptor (H1R) are mainly used to treat allergic reactions. Antihistamines that target the histamine H2-receptor (H2R) are used to treat conditions of the gastrointestinal system.

Some older types of antihistamine drugs are marred by side effects, such as drowsiness and reduced coordination. Also newer types of antihistamine drugs can have unwanted side effects, such as dry mouth and headache. Hence, there is room for further improvement of new ways to treat and prevent allergies.

Various locations of the body of humans and other mammals are inhabited by many different species of bacteria, including a number of different species of lactic acid bacteria. Such bacteria many times coexist with their host giving synergistic beneficial effects of various kinds, nowadays also known to be diverse and dependent upon the actual strain of bacteria. According to the currently adopted definition by Food and Agriculture Organization in the U.S. (FAO) and World Health Organization (WHO), probiotics are "live microorganisms which when administered in adequate amounts confer a health benefit on the host". Nowadays, a number of different bacteria are used as probiotics, for example lactic acid producing bacteria, such as strains of *Lactobacillus* and Bifidobacteria.

One example of a known lactic acid bacterium is *Lactobacillus reuteri*, which is a commensal intestinal Firmicute, and probiotic that is widely prevalent in the gastrointestinal tracts of diverse avian and mammalian species. This organism is considered to be generally recognized as safe (GRAS) and beneficial microbe, and has been used globally as a probiotic for approximately two decades. *L. reuteri* has been reported to suppress pro-inflammatory cytokines in intestinal epithelial cells, monocytes, and intestinal inflammation in different rodent models.

Lee et al. (2004) disclose that lactic acid bacteria can be used as oral allergy-therapeutic means via promoting Th1 cell cytokines, such as IL-2, while suppressing Th2 cell cytokines, such as IL-4 and IL-5.

SUMMARY

It is a general objective to select bacterial strains useful in prophylaxis, inhibition and/or treatment of allergy.

An aspect of the embodiments relates to a method for selecting a bacterial strain for use in prophylaxis, inhibition and/or treatment of an allergy in a mammal. The method comprises screening bacterial strains for capability of producing diacylglycerol kinase (DagK). The method also comprises selecting a bacterial strain which is capable of producing DagK for use in prophylaxis, inhibition and/or treatment of an allergy in a mammal.

Another aspect of the embodiments relates to a bacterial strain capable of producing DagK for use in prophylaxis, inhibition and/or treatment of an allergy in a mammal with the proviso that the bacterial strain is not selected from a group consisting of *Lactobacillus reuteri* strain ATCC PTA-6475 and *L. reuteri* strain ATCC PTA-4659

A further aspect of the embodiments relates to a method of prophylaxis, inhibition and/or treatment of an allergy in a mammal. The method comprises administering a bacterial strain capable of producing DagK to a mammal suffering from or having a risk of developing an allergy with the proviso that the bacterial strain is not selected from a group consisting of *L. reuteri* strain ATCC PTA-6475 and *L. reuteri* strain ATCC PTA-4659.

Additional aspects of the embodiments include *L. reuteri* DSM 32273 for use in prophylaxis, inhibition and/or treatment of an allergy in a mammal, *L. reuteri* ATCC PTA-6475 for use in prophylaxis, inhibition and/or treatment of a food allergy in a mammal, *L. reuteri* ATCC PTA-4659 for use in prophylaxis, inhibition and/or treatment of a food allergy in a mammal and *L. fermentum* ATCC 14931 for use in prophylaxis, inhibition and/or treatment of an allergy in a mammal.

Another aspect of the embodiments relates to an anti-allergy composition comprising a bacterial strain capable of producing DagK and a H1-antihistamine.

Further aspects relate to an anti-allergy composition according to above for use as a medicament and for use in prophylaxis, inhibition and/or treatment of an allergy in a mammal.

The DagK producing bacterial strains of the embodiments are capable of terminating the diacylglycerol (DAG) signaling in the H1R signaling pathway. Accordingly, histamine released in an allergic reaction is inhibited to induce its pro-inflammatory effect via the H1R signaling pathway but is still capable of inducing its anti-inflammatory effect via the H2R signaling pathway.

BRIEF DESCRIPTION OF THE DRAWINGS

The embodiments, together with further objects and advantages thereof, may best be understood by making reference to the following description taken together with the accompanying drawings, in which:

FIG. 5a illustrates a Western blot analysis showing proteins isolated from mouse ileal enteroids of 10 week-old germ free (GF) male mice treated with only media control (LDM-4), WT Lr (WT Lr grown in LDM4), DagK inhibitor and DagK inhibitor with WT Lr for 45 min targeting mammalian phosphorylated PKC (pPKC). 10 μg proteins were loaded into each well of an SDS gel. The pPKC synthesis ratio was obtained by image-J analysis where pPKC of DagK inhibitor treated group was set to 1 and used as baseline. FIG. 5b Mean values of n=3 showing pPKC protein concentration (loaded 10 μg) and quantified by densitometry using image-J. GF control groups were set to 1. *P<0.05, P<0.01, *P<0.001. n=10 mice per group. One-Way analysis of variance with Bonferroni correction.

DETAILED DESCRIPTION

The present embodiments generally relate to selection of bacterial strains, and in particular to selection of bacterial strains useful in prophylaxis, inhibition and/or treatment of allergy, and uses thereof.

The present embodiments have taken a radically different approach in the field of allergy prophylaxis and treatment as compared to the traditional antihistamine approach. In clear contrast to the prior art, the present embodiments are based on selecting and using bacterial strains that are beneficial within prophylaxis, inhibition and/or treatment of allergies. The bacterial strains selected and used according to the embodiments are capable of producing diacylglycerol kinase (Dag K).

DagK is an enzyme that catalyzes the conversion of diacylglycerol (DAG) to phosphatidic acid (PA) utilizing adenosine triphosphate (ATP) as a source of the phosphate. In non-stimulated cells, DagK activity is low allowing DAG to be used for glycerophospholipid biosynthesis. However, on receptor activation of the phosphoinositide pathway, DagK activity increases driving the conversion of DAG to PA. Conversion of DAG to PA depletes DAG, which otherwise may activate protein kinase C (PKC).

Histamine H1-receptor (H1R) downstream signaling is interrupted by DagK synthesis by inhibiting lipid DAG involved in the signaling. Accordingly, DagK-producing bacterial strains as disclosed herein suppress pro-inflammatory effects of released histamine. This in turn allows only histamine H2-receptor (H2R) activation by the histamine produced as a result of an allergic reaction. Such H2R activation promotes anti-inflammatory symptoms.

Thus, a bacterial strain capable of producing DagK causes a suppression of H1R downstream signaling but on the other hand, the histamine released by the allergic reaction induces H2R activation, which in combination suppresses the pro-inflammatory effects of histamine and promotes anti-inflammatory and anti-allergic symptoms.

In bacteria, the enzyme DagK is expressed by the gene dagK.

Figure 1:
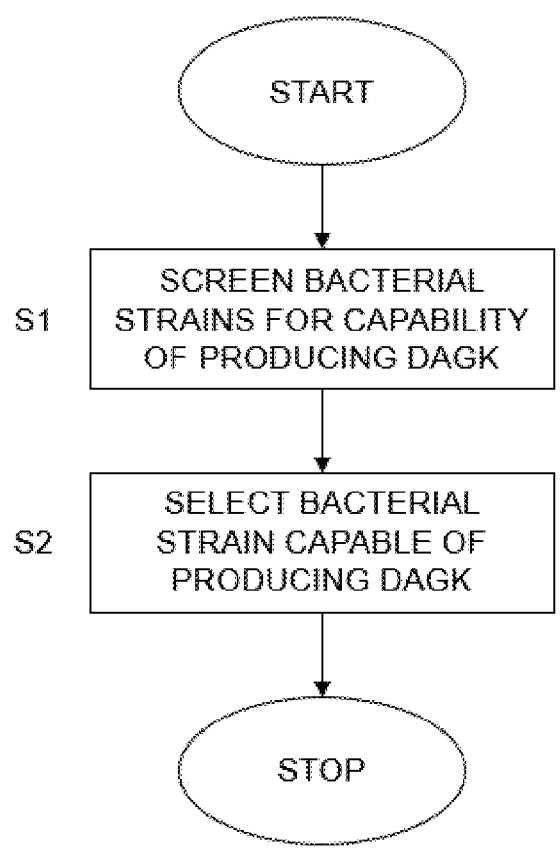
FIG. 1 is a flow chart illustrating a method for selecting a bacterial strain for use in prophylaxis, inhibition and/or treatment of an allergy in a mammal according to an embodiment.

FIG. 1 is a flow chart illustrating a method for selecting a bacterial strain for use in prophylaxis, inhibition and/or treatment of allergy in a mammal. The method comprises screening, in step S1, bacterial strains for capability of producing DagK. The method also comprises selecting, in step S2, a bacterial strain which is capable of producing DagK for use in prophylaxis, inhibition and/or treatment of an allergy in a mammal.

The method as shown in FIG. 1 can thereby be used to identify and select bacterial strains that are useful to prevent, inhibit and/or treat allergy in mammals. The selection criterion is the capability of producing the enzyme DagK, which, as mentioned above, suppresses the pro-inflammatory effects of histamine released as a result of an allergic reaction and promotes the anti-inflammatory effects of the released histamine.

In an embodiment, step S2 in FIG. 1 comprises selecting a bacterial strain which is capable of producing DagK and capable of extracellularly releasing the DagK. Hence, in this embodiment, the bacterial strain selected in step S2 is not only capable of producing DagK but also makes soluble DagK, which is also available extracellularly, i.e., outside of the cells of the selected bacterial strain. This means that the bacterial strains are capable of secreting or otherwise extracellularly releasing DagK.

In an embodiment, screening bacterial strains for capability of producing DagK is assessed by detecting presence of a gene encoding diacylglycerol kinase, such as the dagK gene, in the bacterial strain, either in the genome thereof or in an expression cassette, such as in a plasmid. In such an embodiment, step S1 of FIG. 1 comprises screening the bacterial strains for presence of a gene encoding DagK, such as the dagK gene. Step S2 comprises, in this embodiment, selecting a bacterial strain comprising the gene encoding DagK, such as the dagK gene.

In a particular embodiment, the bacterial strain comprises an active gene encoding DagK. Active with regard to the gene implies that the gene encoding DagK is controlled by a constitutive promoter in the bacterial strain or by an inducible promoter in the bacterial strain, i.e., a promoter that may be activated or induced in the bacterial strain.

There are various techniques available that could be used to detect presence of a gene encoding DagK. Non-limiting, but illustrative techniques, involve polymerase chain reaction (PCR) using primers complementary to portions of the gene encoding DagK or complementary to the promoter of the gene encoding DagK to amplify and detect presence of the amplified deoxyribonucleic acid (DNA) sequence corresponding to the gene encoding DagK, a portion thereof, the promoter of the gene, or a portion thereof. In particular, quantitative polymerase chain reaction (qPCR) can be used to detect presence of a gene encoding DagK. Other techniques involve various DNA sequencing techniques.

In another embodiment, screening bacterial strains for capability of producing DagK is assessed by detecting presence of the DagK enzyme, such as in the cytosol of the bacteria cells or, if the bacterial strain additionally is capable of secreting or extracellularly releasing DagK, in the culture medium, in which the bacterial strain is cultured. In this embodiment, step S1 of FIG. 1 comprises screening the bacterial strains for presence of DagK in a cytosol of the bacterial strains and/or presence of DagK in a respective culture medium in which the bacterial strains are cultured. Step S2 comprises, in this embodiment, selecting a bacterial strain i) comprising DagK in its cytosol and/or ii) for which a culture medium in which the bacterial strain is cultured comprises DagK.

There are various techniques that could be used to detect presence of DagK in the cytosol and/or culture medium of the bacteria cells. Non-limiting, but illustrative, techniques include using anti-DagK antibodies, such as in an enzyme-linked immunosorbent assay (ELISA); protein mass spectrometry, such as peptide mass fingerprinting by matrix-assisted laser desorption/ionization (MALDI) time-of-flight (TOF) and electrospray ionization (ESI) TOF complemented by tandem mass spectrometry (MS/MS) analysis; immuno-electrophoresis; etc.

In an embodiment, the bacterial strains screened and selected in the method of FIG. 1 are bacterial strains generally recognized as safe (GRAS). Accordingly, the bacterial strains should preferably not cause any diseases or deleterious conditions when administered to the mammal in order to prevent, inhibit and/or treat allergy. Hence, the bacterial strains selected according to the method in FIG. 1 are preferably non-pathogenic bacterial strains. Such GRAS bacterial strains are therefore preferably so-called beneficial microbes. A particular example of bacterial strains that are GRAS are probiotic bacteria, such as non-pathogenic probiotic bacteria. Hence, in an embodiment, step S1 in FIG. 1 comprises screening probiotic bacterial strains for capability of producing DagK and step S2 comprises selecting a probiotic bacterial strains which is capable of producing DagK.

In an embodiment, the bacterial strains are lactic acid bacterial strains. In such an embodiment, step S1 comprises screening lactic acid bacterial strains for capability of producing DagK.

Correspondingly, step S2 comprises selecting a lactic acid bacterial strains which is capable of producing DagK.

Lactic acid bacteria, also referred to as lactobacillales, are a clade of Gram-positive, low-GC, acid-tolerant, generally nonsporulating, nonrespiring, either rod- or cocci-shaped bacteria that share common metabolic and physiological characteristics. These bacteria produce lactic acid as the major metabolic end product of carbohydrate fermentation. Genera that comprise the lactic acid bacteria include *Lactobacillus, Leuconostoc, Pediococcus, Lactococcus*, and *Streptococcus*. Lactic acid bacteria can also be found in other genera, such as, *Aerococcus, Carnobacterium, Enterococcus, Oenococcus, Sporolactobacillus, Tetragenococcus, Vagococcus*, and *Weissella*.

Particular preferred bacterial species among *Streptococcus* include *Streptococcus salivarius* and *Streptococcus termophilus*.

In a particular embodiment, the bacterial strains are *S. salivarius* or *S. termophilus* strains. In this embodiment, step S1 of FIG. 1 comprises screening *S. salivarius* or *S. termophilus* strains for capability of producing DagK and step S2, correspondingly, comprises selecting a *S. salivarius* or *S. termophilus* strain which is capable of producing DagK.

In a particular embodiment, step S2 comprises selecting a *S. salivarius* or *S. termophilus* strain which is capable of producing DagK for use in prophylaxis, inhibition and/or treatment of a pollen allergy in a mammal.

A currently preferred genus is *Lactobacillus*.

*Lactobacillus* include several species including *L. acetotolerans, L. acidifarinae, L. acidipiscis, L. acidophilus, L. agilis, L. algidus, L. alimentarius, L. amylolyticus, L. amylophilus, L. amylotrophicus, L. amylovorus, L. animalis, L. antri, L. apodemi, L. aviaries, L. bifermentans, L. brevis, L. buchneri, L. camelliae, L. casei, L. catenaformis, L. ceti, L. coleohominis, L. collinoides, L. cornposti, L. concavus, L. coryniformis, L. crispatus, L. crustorum, L. curvatus, L. delbrueckii* subsp. *bulgaricus, L. delbrueckfi* subsp. *elbrueckii, L. delbrueckfi* subsp. *lactis, L. dextrinicus, L. diolivorans, L. aqui, L. equigenerosi, L. farraginis, L. farciminis, L. fermentum, L. fornicalis, L. fructivorans, L. frumenti, L. fuchuensis, L. gallinarum, L. gasseri, L. gastricus, L. ghanensis, L. graminis, L. hammesii, L. hamster, L. harbinensis, L. hayakitensis, L. helveticus, L. hilgardii, L. homohiochii, L. finers, L. ingluviei, L. intestinalis, L. jensenii, L. johnsonii, L. kalixensis, L. kefiranofaciens, L. kefiri, L. kimchi, L. kitasatonis, L. kunkeei, L. leichmannii, L. lindneri, L. malefermentans, L. mall, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracasei, L. paracollinoides, L. parafarraginis, L. parakefiri, L. paralimentarius, L. paraplantarum, L. pentosus, L. perolens, L. plantarum, L. pontis, L. protectus, L. psittaci, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmoldensis, L. vini, L. vitulinus, L. zeae*, and *L. zymae*. In an embodiment, the bacterial strains are lactic acid bacterial strains having GRAS status, being non-pathogenic and selected among the above presented group of *Lactobacillus* species.

In a particular embodiment, the bacterial strains are *L. reuteri* strains. In this embodiment, step S1 of FIG. 1 comprises screening *L. reuteri* strains for capability of producing DagK and step S2, correspondingly, comprises selecting a *L. reuteri* strain which is capable of producing DagK.

In a particular embodiment, step S2 comprises selecting a *L. reuteri* strain which is capable of producing DagK for use in prophylaxis, inhibition and/or treatment of a food allergy in a mammal.

In another particular embodiment, the bacterial strains are *L. fermentum* strains. In this embodiment, step S1 of FIG. 1 comprises screening *L. fermentum* strains for capability of producing DagK and step S2, correspondingly, comprises selecting a *L. fermentum* strain which is capable of producing DagK.

In a particular embodiment, step S2 comprises selecting a *L. fermentum* strain which is capable of producing DagK for use in prophylaxis, inhibition and/or treatment of a pollen allergy in a mammal.

In an embodiment, the bacterial strains are grown in presence of DAG in order to achieve pre-activated bacteria strains already expressing DagK before freeze-drying or lyophilizing of the bacteria. Hence, in this embodiment the method further comprises culturing the bacterial strains in presence of DAG.

Another aspect of the embodiments relates to a bacterial strain capable of producing DagK for use in prophylaxis, inhibition and/or treatment of an allergy in a mammal with the proviso that the bacterial strain is not selected from a group consisting of *L. reuteri* strain ATCC PTA-6475 and *L. reuteri* strain ATCC PTA-4659.

In an embodiment, the allergy is selected from a group consisting of a food allergy and a pollen allergy. In a particular embodiment, the allergy is a food allergy and preferably a food allergy selected from a group consisting of peanut allergy, milk (lactose or milk protein) allergy, egg allergy, tree nuts allergy, fish allergy, shellfish allergy, soy allergy, and wheat (gluten) allergy.

Non-limiting examples of pollen allergies include allergy against pollen from pine (*Pinus*), birch (*Betula*), alder (*Alnus*), cedar, hazel (*Corylus*), hornbeam (*Carpinus*), horse chestnut (*Aesculus*), willow (*Salix*), poplar (*Populus*), plane (*Platanus*), linden/lime (*Tilia*), olive (*Olea*), sugi (*Cryptomeria japonica*), hinoki (*Chamaecyparis obtusa*), ryegrass (*Lolium* sp.), timothy (*Phleum pratense*), ragweed (*Ambrosia*), plantain (*Plantago*), nettle/parietaria (Urticaceae), mugwort (*Artemisia Vulgaris*), Fat hen (*Chenopodium*), and sorrel/dock (*Rumex*).

The DagK producing bacterial strains of the embodiments can be used to treat allergy in the mammal. Treat as used herein does not necessarily imply that the mammal becomes 100% symptom free following administration of the bacterial strains of the embodiments to the mammal. Treat also encompasses reducing the symptoms of the allergy in the mammal. Hence, the bacterial strains of the embodiments can be used to inhibit or suppress allergy in the mammal.

The bacterial strains of the embodiments could also, or alternatively, be used in prophylaxis, i.e., preventing or at least reducing the risk of a mammal to develop allergy. The mammal could, for instance, have a predisposition to allergy, such as a genetic or heredity predisposition to allergy. The bacterial strains of the embodiments could then be administered to such a mammal to prevent or at least reduce the risk of the mammal suffering from allergy or developing an allergic reaction.

In a particular embodiment, the mammal to which the bacterial strains of the embodiments can be administered is preferably a human. The bacterial strains of the embodiments could also be used in veterinary applications, i.e., administered to non-human mammals. Non-limited examples of such non-human mammals include dog, cat, horse and cow.

In an embodiment, the bacterial strain is a bacterial strain capable of producing DagK and capable of extracellularly releasing, such as secreting, DagK.

In an embodiment, the bacterial strain is a lactic acid bacterial strain capable of producing DagK. In a particular embodiment, the lactic acid bacterial strain is a lactic acid bacterial strain capable of producing DagK selected from a group consisting of *Lactobacillus, Leuconostoc, Pediococcus, Lactococcus, Streptococcus, Aerococcus, Carnobacterium, Enterococcus, Oenococcus, Sporolactobacillus, Tetragenococcus, Vagococcus,* and *Weissella*. In an embodiment, the lactic bacterial strain capable of producing from DagK is selected from a group consisting of *Lactobacillus, Leuconostoc, Pediococcus, Lactococcus* and *Streptococcus*.

In an embodiment, the bacterial strain is a *L. reuteri* strain capable of producing DagK. In a particular embodiment, the *L. reuteri* strain capable of producing DagK is for use in prophylaxis, inhibition and/or treatment of a food allergy in a mammal.

In another embodiment, the bacterial strain is a *L. fermentum* strain capable of producing DagK. In a particular embodiment, the *L. fermentum* strain capable of producing DagK is for use in prophylaxis, inhibition and/or treatment of a pollen allergy in a mammal.

In yet another embodiment, the bacterial strain is a *S. salivarius* or *S. termophilus* strain capable of producing DagK. In a particular embodiment, the *S. salivarius* or *S. termophilus* strain capable of producing DagK is for use in prophylaxis, inhibition and/or treatment of a pollen allergy in a mammal.

Yet another aspect of the embodiments relates to use of a bacterial strain capable of producing DagK in the manufacture of a medicament for prophylaxis, inhibition and/or treatment of an allergy in a mammal, with the proviso that the bacterial strain is not selected from a group consisting of *L. reuteri* strain ATCC PTA-6475 and *L. reuteri* strain ATCC PTA-4659.

A further aspect of the embodiments relates to a method of prophylaxis, inhibition and/or treatment of an allergy in a mammal. The method comprises administering a bacterial strain capable of producing DagK to a mammal suffering from or having a risk of developing an allergy, with the proviso that the bacterial strain is not selected from a group consisting of *L. reuteri* strain ATCC PTA-6475 and *L. reuteri* strain ATCC PTA-4659.

An appropriate mode of administration and formulation of the bacterial strains is chosen depending on the site where local production of DagK is desired. A preferred mode of administration is oral. Other modes of administration include nasal, intraocular, topical or some other form of local administration to the skin, rectum, nose, eyes, vagina or gums, or intravenous, subcutaneous or intramuscular injection.

Oral administration of the bacterial strains of the embodiments may be particularly preferred to prevent, inhibit and/or treat food allergy in a mammal. In such a case, the bacterial strains will, due to the mode of administration, be close the intestinal epithelium and can thereby, by the production of DagK by the bacterial strains, modify the lipid signaling to cause changes in the immune biomarkers to have a local impact on the inflammatory or allergic responses.

Nasal administration of the bacterial strains of the embodiments may be particularly preferred to prevent, inhibit and/or treat pollen allergy in a mammal. In such a case, the bacterial strains will, due to the mode of administration, be close the respiratory epithelium and can thereby, by the production of DagK by the bacterial strains, modify the lipid signaling to cause changes in the immune biomarkers to have a local impact on the inflammatory responses or allergic responses.

Appropriate doses of the strains as defined herein can readily be chosen depending on the allergy to be treated, the mode of administration and the formulation concerned. For example, a dosage and administration regime is chosen such that the bacteria administered to the subject in accordance with the present invention can result in desired therapeutic effects, prophylactic effects or health benefits. Thus, preferably the dosage is a therapeutically or prophylactically effective dosage, which is appropriate for the type of mammal and allergy being treated. For example, daily doses of $10^4$ to $10^{10}$, for example $10^5$ to $10^9$, or $10^6$ to $10^8$, or $10^8$ to $10^{10}$ total CFUs of bacteria may be used. A preferred daily dose is around $10^8$ total CFUs, e.g., $10^7$ to $10^9$ or $10^8$ to $10^9$.

Allergies are generally correlated with an increased histamine release with pro-inflammatory symptoms. Thus, DagK producing bacterial strains of the embodiments could be a great therapeutic approach to suppress inflammation caused by the histamine released during the allergic reaction in a more natural way. This means that the bacterial strains of the embodiments capable of producing DagK can avoid side effects caused by antihistamine drugs.

A prophylactic or therapeutic anti-allergy effect can be achieved by the bacterial strains of the embodiments alone, i.e., as the sole anti-allergy active agent. However, the bacterial strains of the embodiments could be combined with other anti-allergy drugs, such as antihistamines, to form a composition comprising the bacterial strains and at least one antihistamine, optionally together with a pharmaceutically acceptable carrier, diluent, excipient or solvent. A combined treatment can also be achieved by separately administering the bacterial strains of the embodiments and at least one antihistamine to the mammal suffering from or running a risk of suffering from allergy.

An advantage of a combined treatment, in which a DagK producing bacterial strain is combined with at least one antihistamine, is that the required dose of the at least one antihistamine can be reduced to as compared to solely administering the at least one antihistamine. Such a reduction in the antihistamine dose can thereby avoid or at least minimize any side effects associated with the at least one antihistamine while still achieving sufficient anti-allergy effect.

Accordingly, in an embodiment, an amount of the at least one antihistamine in the composition is preferably less than 90%, such as by weight, as compared to an amount of the at least one antihistamine in a composition comprising the at least one antihistamine as the sole anti-allergy agent(s), i.e., lacking any bacterial strain of the embodiments. In various embodiments, the amount of the at least one antihistamine in the composition is preferably less than 80%, less than 70%, less than 60%, less than 50%, less than 40%, less than 30%, less than 20%, or less than 10%, such as by weight, as compared to an amount of the at least one antihistamine in a composition comprising the at least one antihistamine as the sole anti-allergy agent(s), i.e., lacking any bacterial strain of the embodiments.

Non-limiting, but illustrative, examples of antihistamines that can be used together with a DagK producing bacterial strain in a combined treatment include H1-antishistamines, such as H1R antagonists and/or H1R inverse agonists.

Illustrative examples of H1R antagonists include acrivastine, azelastine, bilastine, bromodiphenhydramine, brompheniramine, buclizine, carbinoxamine, cetirizine (for instance sold under the name ZYRLEX®, VIALERG®, ACURA®), chlorodiphenhydramine, chlorphenamine, chlorpromazine, clemastine, cyclizine, cyproheptadine, dexbrompheniramine, dexchlorpheniramine, dimenhydrinate, dimetindene, diphenhydramine, doxylamine, ebastine (for instance sold under the name KESTINE®), embramine, fexofenadine (for instance sold under the name ALLEGRA®, ALTIFEX®), hydroxyzine, loratadine (for instance sold under the name CLARITYN®), meclizine, mirtazapine, olopatadine, orphenadrine, phenindamine, pheniramine, phenyltoloxamine, promethazine, quetiapine, rupatadine, tripelennamine and triprolidine.

Illustrative examples of H1R inverse agonists include cetirizine, levocetirizine, desloratadine (for instance sold under the name FLYNISE®) and pyrilamine.

Accordingly, an aspect of the embodiments relates to an anti-allergy composition comprising a bacterial strain capable of producing DagK and a H1-antihistamine.

In an embodiment, the H1-antihistamine is selected from a group consisting of cetirizine, ebastine, fexofenadine, loratadine and desloratadine.

In an embodiment, the bacterial strain is not selected from a group consisting of *L. reuteri* strain ATCC PTA-6475 and *L. reuteri* strain ATCC PTA-4659.

Further aspects of the embodiments relates to an anti-allergy composition for use as a medicament and for use in prophylaxis, inhibition and/or treatment of an allergy in a mammal.

Appropriate doses of the strains as defined herein in a combined treatment can readily be chosen depending on the allergy to be treated, the mode of administration, the formulation concerned and the at least one antihistamine that used in the combined treatment. For example, a dosage and administration regime is chosen such that the bacteria and antihistamine(s) administered to the subject in accordance with the present invention can result in desired therapeutic effects, prophylactic effects or health benefits. Thus, preferably the dosage is a therapeutically or prophylactically effective dosage, which is appropriate for the type of mammal and allergy being treated. The daily doses for the bacteria mentioned in the foregoing can be used be used in the combined treatment. It is also possible to use lower daily doses for the combined treatment since the bacteria are combined with at least one antihistamine.

The bacterial strains can also be used as an adjuvant in oral immunotherapy for the treatment of food allergy, such as peanut allergy.

Experimental data as presented herein show that *L. reuteri* DSM 32273 (deposited under the Budapest Treaty at the DSMZ-Deutsche Sammlung von Mikroorganismen and Zellkulturen GmbH (Inhoffenstrasse 7B, D-38124 Braunschweig, Germany) on Mar. 8, 2016), *L. reuteri* ATCC PTA-6475 (deposited under the Budapest Treaty at the American Type Culture Collection (10801 University Blvd, Manassas, VA 20110-2209, U.S.) on Dec. 21, 2004) and *L. reuteri* ATCC PTA-4659 (deposited under the Budapest Treaty at the American Type Culture Collection (10801

University Blvd, Manassas, VA 20110-2209, U.S.) on Sep. 11, 2002) are *L. reuteri* strains capable of producing DagK. Accordingly, these *L. reuteri* strains can be used in prophylaxis, inhibition and/or treatment of an allergy in a mammal as disclosed herein. In a particular embodiment, the allergy is a food allergy.

Thus, an aspect of the embodiments relates to a *L. reuteri* strain DSM 32273 for use in prophylaxis, inhibition and/or treatment of an allergy in a mammal. In a particular embodiment, the allergy is a food allergy.

Other aspects of the embodiments relates to a *L. reuteri* strain ATCC PTA-6475 and/or a *L. reuteri* strain ATCC PTA-4659 for use in prophylaxis, inhibition and/or treatment of a food allergy in a mammal.

The *L. reuteri* strains DSM 32273, ATCC PTA-6475 and ATCC PTA-4659 could be used separately or as a composition of at least two of the *L. reuteri* strains, such as *L. reuteri* DSM 32273 and ATCC PTA-6475, *L. reuteri* DSM 32273 and ATCC PTA-4659, *L. reuteri* ATCC PTA-4659 and ATCC PTA-6475, or *L. reuteri* DSM 32273, ATCC PTA-6475 and ATCC PTA-4659.

In an embodiment, *L. fermentum* ATCC 14931 is a *L. fermentum* strain capable of producing DagK. Accordingly, *L. fermentum* ATCC 14931 can be used in prophylaxis, inhibition and/or treatment of an allergy in a mammal as disclosed herein. In a particular embodiment, the allergy is a pollen allergy.

The *L. fermentum* strain ATCC 14931 could be used separately or as a composition of at least one of the above listed DagK-producing *L. reuteri* strains. Such a composition could, then, include *L. fermentum* ATCC 14931 and *L. reuteri* DSM 32273, *L. fermentum* ATCC 14931 and *L. reuteri* ATCC PTA-6475, *L. fermentum* ATCC 14931 and *L. reuteri* ATCC PTA-4659, *L. fermentum* ATCC 14931, *L. reuteri* DSM 32273 and ATCC PTA-6475, *L. fermentum* ATCC 14931, *L. reuteri* DSM 32273 and ATCC PTA-4659, *L. fermentum* ATCC 14931, *L. reuteri* ATCC PTA-4659 and ATCC PTA-6475, or *L. fermentum* ATCC 14931, *L. reuteri* DSM 32273, ATCC PTA-6475 and ATCC PTA-4659.

In a particular embodiment, the method of FIG. 1 comprises screening bacterial strains, other than 15 *L. reuteri* DSM 32273, ATCC PTA-4659 and ATCC PTA-6475, and *L. fermentum* ATCC 14931, for capability of producing DagK. The method also comprises selecting a bacterial strain, other than *L. reuteri* DSM 32273, ATCC PTA-4659 and ATCC PTA-6475, and *L. fermentum* ATCC 14931, which is capable of producing DagK for use in prophylaxis, inhibition and/or treatment of an allergy in a mammal.

EXAMPLES

Example 1

Quantification of dagK mRNA Gene Expression by qRT-PCR

Wild type (WT) *Lactobacillus reuteri* ATCC PTA-6475, hdcA mutant of *L. reuteri* ATCC PTA-6475 (previously described in Thomas et al., 2012), WT *L. reuteri* ATCC PTA-4659 and WT *L. reuteri* DSM 17938 (deposited under the Budapest Treaty at the DSMZ-Deutsche Sammlung von Mikroorganismen and Zellkulturen GmbH (Mascheroder Weg 1 b, D-38124 Braunschweig, Germany) on Jan. 30, 2006) were grown in the MRS media overnight at 37° C. and were cultured under strict anoxic conditions $N_2/CO_2$ (80/20; v/v) as the gas phase. 100 µl of fresh culture was incubated into 10 ml of *lactobacillus* defined media 4 (LDM4). The cultures were maintained in mini bioreactors at 37° C. under strict anoxic conditions. The samples were collected at 3 hours, 6 hours, 24 hours and 48 hours. The bacterial pellet was obtained by treating the culture at 6000×g for 10 min at 4° C. The pellet was treated with RNase later. mRNA from the bacterial cells were extracted by Trizol separation kit. 500 ng of mRNA from each group was used to convert mRNA into cDNA. The treated cDNA was diluted 1:2 and was used to run qRT-PCR. The Stratagene Mx3000p (Agilent Technologies GmbH, USA) qRT-PCR was used for amplification and fluorescent data collection. The master mix consisted of 12.5 µl Power SYBR Green 2000 (ABI systems, USA), 0.5 µl of each primer (DAGK-L.r-F: GCGT-GAGTCCATAACCGTCT (SEQ ID NO: 9) and DAGK-L.r-R: ATGGCTGCTGAAATTCCTGT (SEQ ID NO: 10), 10 µM), 1 µl of sample and adjusted with water to a final volume of 25 µl per well. After PCR amplification, the specificity of the primers was checked by inspecting the melting curve and determining the size of the amplicon by agarose gel electrophoresis (1%). Relative mRNA target gene expression levels (Ratio=$[(E_{target})^{dCPtarget(control-sample)}]/[(E_{ref.})^{dCPref.(control-sample)}]$) were normalized to the house keeping gene rpoB and used as a reference. Subsequently, mRNA obtained from 3 hours culture of each bacterium were set to 1.0 and used as the calibrator to identify the relative mRNA fold difference of same bacterial strain at different time points like 6 hours, 24 hours and 48 hours of *L. reuteri* ATCC PTA-6475, ATCC PTA-4659 and DSM 17938.

Figure 2:
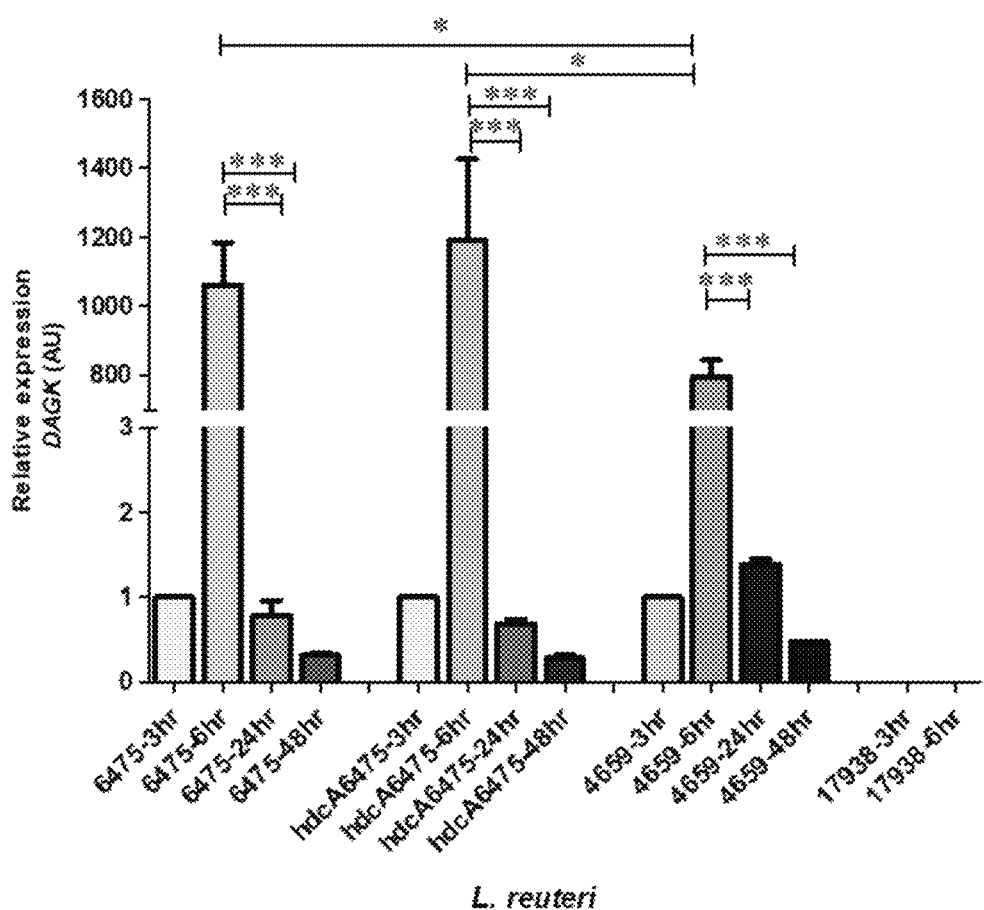
FIG. 2 illustrates that *L. reuteri* wild-type (WT) and hdcA mutant ATCC PTA-6475 and ATCC PTA-4659 produce DagK. Relative mRNA target gene expression levels normalized to the house keeping gene rpoB are presented from 3, 6, 24 and 48 hours culture of each bacterium. mRNA obtained from 3 hours culture of each bacterium were set to 1.0 and used as calibrator to identify the relative mRNA fold difference.

FIG. 2 illustrates the results of the dagK gene expression experiments. The figure shows an increased dagK expression by both WT and hdcA mutant *L. reuteri* ATCC PTA-6475 together with *L. reuteri* ATCC PTA-4659. However, *L. reuteri* DSM17938 lacked dagK expression, i.e., was not capable of producing DagK. Interestingly dagKmRNA expression was expressed very high during the elongation phase of the bacteria. From the repetition experiments 12 hours incubation time points was selected since it showed similar expression like 6 hours.

Example 2

LC-MSIMS for Detecting DagK Protein in the Bacterial Culture Supernatants

According to the literatures DagK is believed to have soluble isoforms in gram positive bacteria. We hypothesized that DagK is released from *L. reuteri* ATCC PTA-6475 and it interacts with the host intestinal epithelial lipid signaling and suppress pro-inflammatory effects of released histamine due to an allergic reaction and also promotes anti-inflammatory behavior. When we mutated the dagK gene in *L. reuteri* ATCC PTA-6475 (mutants were created by RecT-mediated single strand recombineering as described in van Pijkeren and Britton (2012) and is adapted to mutate the dagKgene using dagKtargeted oligos) and colonized our germ-free (GF) mice with the DagK mutant *L. reuteri* ATCC PTA-6475 we did not see a suppression of IL-6 and IL-la like we observed in the germ-free mice colonized with wild-type *L. reuteri* ATCC PTA-6475. The basal pro-inflammatory cytokine levels were significantly suppressed. Histamine released due to an allergic reaction can activate H1R and H2R. However, H1R downstream signaling is interrupted by DagK synthesis in *L. reuteri* by inhibiting lipid DAG involved in the signaling and thereby suppress pro-inflammatory effect of histamine. This allows only H2R activation, which is known to promote anti-inflammatory symptoms.

For dagK to show any positive effect on host immune response host-DAG lipid should be expressed. For DAG to be activated H1R signaling must be activated. That is why when we mutated dagK in *L. reuteri* and colonized the mice we did not see pro-inflammatory cytokine suppression. This was additionally confirmed with PKC and PKA activation.

Figure 3:
FIG. 3 illustrates *L. reuteri* DagK amino acid sequence (SEQ ID NO: 13). The amino acid sequence of *L. reuteri* DagK is shown together with trypsin cleavage sites (vertical lines). The bold amino acids indicate peptide sequences obtained following such trypsin treatment. The black bars indicate peptide sequences found in LC-MS/MS experiments.
Figure 4:
FIG. 4 illustrates *L. reuteri* DagK amino acid sequence (SEQ ID NO: 13). The bold amino acids indicate peptide sequences obtained. The black bars indicate peptide sequences found in LC-MS/MS experiments.
Figure 4:

To further show whether DagK isoforms are secreted or not from *L. reuteri* we performed bacterial cell culture experiments. 100 µl of overnight MRS grown *L. reuteri* ATCC PTA-6475 at 37° C. under anoxic conditions were added to 10 ml LDM4 media in the presence and absence of DAG and left at 37° C. for 12 hours under anoxic conditions. The bacterial cells were removed by centrifugation at 6000× g, 10 min at 4° C. 1:1 ratio of proteinase and protein kinase inhibitor was added to the supernatant. The supernatants were filtered by 0.22 µm filter to remove traces of bacteria. Since DagK is a 10-13 kDa protein, it is necessary to reduce the background. Therefore the supernatant was processed with 50 kDa filtrate. The flow through was added to the 3 kDa filtrate and spun at 5000×g for 30 min. The concentrate on the upper phase was used to run the LC-MS/MS after tryptic digestion. FIG. 3 illustrates the amino acid sequence of DagK protein from *L. reuteri* ATCC PTA-6475 together with trypsin digestion or cleavage sites (Tryps). FIG. 4 illustrates the amino acid sequence of DagK protein from *L. reuteri* ATCC PTA-6475 when DAG was present in the cell culture media.

The results of the LC-MS/MS experiment is presented in Table 1 and 2 and FIGS. 3 and 4. The sequences that match the *L. reuteri* DagK protein were found in the supernatant. Accordingly, *L. reuteri* ATCC PTA-6475 was capable of producing and secreting the DagK protein. Interestingly, *L. reuteri* secreted higher levels of DagK in the presence of DAG in cell culture media compared to its absence. However, we can detect DagK in the presence and absence of DAG but their concentrations differ. Media control stayed negative.

TABLE 1

LC-MS/MS Results of Trypsin Treatment of Supernatant from *L. reuteri* ATCC PTA-6475

| Peptide | -10lgP | Mass | Length | ppm | m/z | RT | Scan | #Spec |
|---|---|---|---|---|---|---|---|---|
| A | 18.31 | 833.3813 | 6 | -6.4 | 417.6953 | 58.33 | 139 | 3 |
| B | 14.72 | 971.5287 | 11 | -62.2 | 486.7414 | 63.33 | 432 | 1 |
| C | 9.09 | 884.4352 | 7 | 35 | 443.2404 | 72.68 | 1088 | 1 |
| D | 8.83 | 1487.774 | 13 | -64.8 | 744.8461 | 52.15 | 42 | 1 |
| E | 7.94 | 996.4447 | 7 | 30.9 | 499.245 | 64.98 | 549 | 1 |
| F | 5.73 | 2710.64 | 27 | -79.9 | 678.6131 | 86.5 | 1394 | 1 |

Peptides A-F in Table 1:
| | | |
|---|---|---|
| A | EERNMR | SEQ ID NO: 1 |
| B | DVAAGGVLISA | SEQ ID NO: 2 |
| C | DKHQTEK | SEQ ID NO: 3 |
| D | NMRYHLLAACLAI | SEQ ID NO: 4 |
| E | EERNMRY | SEQ ID NO: 5 |
| F | KAKDVAAGGVLISAIFSVLVGLIIFIP | SEQ ID NO: 6 |

TABLE 2

LC-MS/MS Results of Trypsin Treatment of Supernatant from *L. reuteri* ATCC PTA-6475 when DAG was present in the cell culture media

| Peptide | -10lgP | Mass | Length | ppm | m/z | RT | Scan | #Spec |
|---|---|---|---|---|---|---|---|---|
| G | 23.58 | 700.3755 | 8 | 1.7 | 701.384 | 24.55 | 15840 | 1 |
| H | 15.34 | 4515.4473 | 39 | -1.3 | 1129.8677 | 30.12 | 18496 | 1 |

Peptides G-H in Table 2:
| | | |
|---|---|---|
| G | DVAAGGVL | SEQ ID NO: 7 |
| H | NMRYHLLAACLAIIMSILLHISAMEWLWILLAIFVVFTS | SEQ ID NO: 8 |

Example 3

Identification of Strains Capable of Producing DagK

The bacteria are cultivated on MRS plates for 16 h at 37° C. in anaerobic atmosphere. Bacterial colonies are collected with a sterile plastic loop and suspended in 100 µl of sterile water (PCR quality). Alternatively, DNA can be prepared from the bacterial culture using any suitable method, see for instance Example 1.

Presence of the dagK gene is examined by PCR, e.g., by using PuReTaq Ready To Go PCR beads (GE HealthCare) and the primer pair dagK_LrF (TGGACTCACGCGATAAACATCA, SEQ ID NO: 11) and dagK_LrR (ACAATCAAATCTGTAACAGCTTCG, SEQ ID NO: 12), 0.4 mM of each. Bacterial suspension or DNA preparation (0.5 µl) is added to the PCR mix and the PCR reaction is performed by running the program 95° C., 5 min; 30× (95° C., 30 s; 58° C., 30 s; 72° C., 30 s); 72°, 10 min. The PCR products are separated and visualized by using standard agarose gel electrophoresis and the sequence is determined by standard Sanger sequencing using the forward primer (dagK_LrF) used for the PCR.

Example 4

Analysis of *Lactobacillus reuteri* DSM 32273 Capable of Producing DagK

*Lactobacillus reuteri* DSM 32273 bacteria were grown over night in MRS broth at 37° C. The bacterial suspensions were centrifuged at 3500 rpm for 5 min and 1 µl of the pellet was suspended in 100 µl of PBS.

The PCR analysis of dagK gene in *L. reuteri* DSM 32273 was done as described in Example 3.

The results showed that *L. reuteri* DSM 32273 was positive for the gene encoding histidine decarboxylase and the dagK gene, see Table 3. The bacterial strains *L. reuteri* ATCC PTA-6475 and DSM 17938 were included as controls.

TABLE 3

Results from the PCR Analysis Showing the Species, Strain and Host Origin of the Tested bacteria.

| Species | Strain | Host origin | Presence of dagK gene |
|---------|--------|-------------|----------------------|
| L. reuteri | ATCC PTA-6475 | Human | + |
|  | DSM 17938 | Human | − |
|  | DSM 32273 | Human | + |

Example 5

Manufacture of a Probiotic Product for Use in Pollen Allergy

In this example, a probiotic product for use in pollen allergy is manufactured. The strain *L. fermentum* ATCC 14931 is selected based on its capability to produce DagK as analyzed from the published genome sequence. The *L. fermentum* strain is grown and lyophilized, using standard methods for growing *Lactobacillus* in the industry. The product is an oil-based formulation made for good stability and shelf life. The unique feature of production process is the step of drying the oil by placing it under vacuum to remove most of the water in the oil and to increase the stability in the formulation. The oil used in the invention herein is a pure edible vegetable oil, preferably sunflower oil and medium-chain triglyceride.

Mixing of Ingredients.

1. Mix the medium-chain triglyceride, for example, Akomed R (Karlshamns AB, Karlshamn Sweden), and sunflower oil, for example, Akosun (Karlshamns AB, Karlshamn Sweden) with silicon dioxide, Cab-o-sil MSP, MSP, Cabot) in a Bolz mixing machine/tank (Alfred BOLZ Apparatebau GmbH, Wangen im Allgäu, Germany).

2. Homogenization. A Sine pump and dispax (Sine Pump, Arvada, Colorado) are connected to the Bolz mixer and the mixture is homogenized.

3. Vacuum-drying. The mixture is dried under 10 mBar vacuum in the Bolz tank, for 12 hours.

4. Adding *Lactobacillus fermentum*. About 20 kg of dried oil mixture is moved to a 50 liter stainless steel vessel. *L. fermentum* powder, preferably freeze-dried; the amount of *L. fermentum* used would vary depending on the amount wanted in the oil, but one example would be to add 0.2 kg of culture having $10^{11}$ CFU per g, is added. It is mixed slowly until homogenous.

5. Mixing. The premix with *L. fermentum* is brought back to the Bolz mixer.

6. Discharging. The suspension is discharged to a 200 liter glass vessel, and covered with nitrogen.

The suspension is held in the vessel until filling in spray bottles to be used for nasal administration to a human for the prevention or treatment of pollen allergy.

Example 6

Manufacture of a Probiotic Product for Use in Food Allergy

In this example, *Lactobacillus reuteri* DSM 32273 is selected based on its capability to produce DagK in order to add the strain to a tablet for use in the prevention, inhibition and/or treatment of food allergy in humans. The *L. reuteri* strain is grown and lyophilized, using standard methods for growing *Lactobacillus* in the industry.

The following steps illustrate an example of a manufacturing process for tablets containing the selected bacterial strain, including glucose encapsulation. It is understood that excipients, fillers, flavors, encapsulators, lubricants, anticaking agents, sweeteners and other components of tablet products as are known in the art, may be used without affecting the efficacy of the product:

1. Melting. Melt SOFTISAN™ 154 (SASOL GMBH, Bad Homburg, Germany) in a vessel and heat it to 70° C. to assure complete disruption of the crystalline structure. Then cool it down to 52-55° C. (just above its hardening point).

2. Granulation. Transfer *Lactobacillus reuteri* freeze-dried powder to a Diosna high-shear mixer/granulator, or equivalent. Add slowly during approximately 1 minute the melted SOFTISAN™ 154 to the *L. reuteri* powder. Use chopper during the addition.

3. Wet-sieving. Immediately after the granulation, pass the granules through a 1-mm sieving net by using a Tornado mill. The sieved granulate is packed in alupouches, made out of PVC-coated aluminum foil, sealed with a heat sealer to form a pouch, together with desiccant pouch, and stored refrigerated until mixing. The granulated batch is divided for two tablet batches.

4. Add encapsulated D-Glucose (G8270, >99.5% glucose, Sigma), encapsulated using standard microencapsulating methods as known in the art. The amount of sugar is dependent on the total CFU of the added powder of dry *L. reuteri*, a standard level can be 1 gram of sugar per total CFU of $10^8$ of bacteria but this could also be varied down to 0.1 gram or 0.01 gram up to 10 gram even up to 100 gram of sugar.

5. Mixing. Mix all the ingredients in a mixer, to a homogenous blend.

6. Compression. Transfer the final blend to the hopper of a rotary tablet press and compress tablets with a total weight of 765 mg, in a Kilian compressor.

7. Bulk packaging. The tablets are packed in alu-bags together with a drying pouch of molecular sieve. The alu-pouch is put in a plastic bucket and stored in a cool place at least one week, before final package. The use of SOFTISAN™, a hydrogenated palm oil, enables the *Lactobacillus* cells to be encapsulated in fat and environmentally protected.

As stated above, the product of the embodiments may be in forms other than tablet, and standard methods of preparing the underling underlying product as are known in the art are beneficially used to prepare the product of the invention including the selected *L. reuteri* culture.

Example 7

Mouse Enteroid Experiment to Explore Mammalian Intestinal Epithelial DAG and pPKC Signaling Mouse enteroids (contains only intestinal epithelial layer) were derived from 10 week-old germ free (GF) BALB/c mouse. The enteroids were grown to form a monolayer and were induced with LDM4 media (control), wild-type *L. reuteri* PTA-6475 conditioned media (50 to 3 kDa cut off), diacylglycerol kinase (DGK) inhibitor (2 µM) only or DGK inhibitor (2 µM) with wild-type *L. reuteri* PTA-6475 conditioned media (CM; 50 to 3 kDa cut off). DGK inhibitor (R59-022; 6-[2-(4-[(4-fluorophenyl)phenylmethylene]-1-piperidinyl)ethyl]-7-methyl-5H-thiazolo-[3,2-a]pyrimidine-5-one) was added 2 hours prior to the addition of conditioned media on enteroids to prevent the mammalian DGK activation and after 2 hours the enteroids were washed and treated with conditioned media or only LDM4 media with or without DGK inhibitor respectively. The proteins were collected after 45 min of incubation to perform Western blot.

Figure 5A:
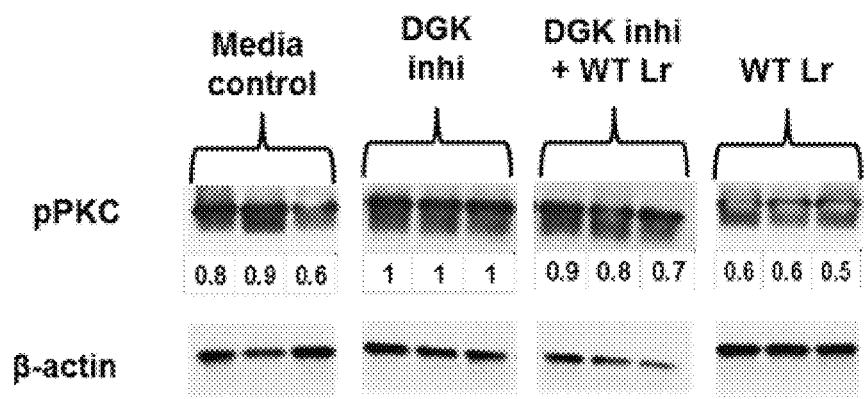
FIGS. 5a and 5b illustrate that a commercially available DagK inhibitor (DGK inhi) prevents *L. reuteri* derived-DagK mediated protein kinase C (PKC) phosphorylation in mouse enteroids.
Figure 5B:
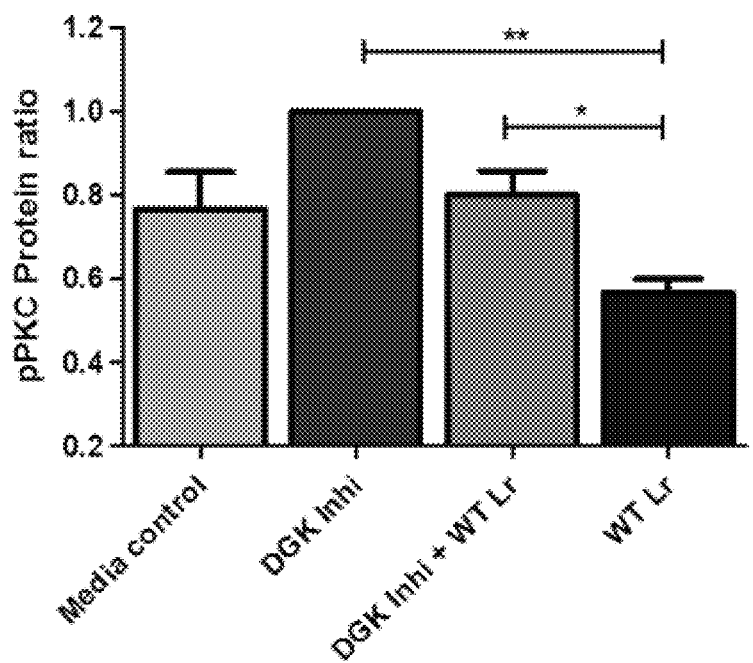

The enteroids treated with a DGK inhibitor yielded increased PKC phosphorylation in the presence of wild-type (WT) *L. reuteri* PTA-6475 conditioned media, while enteroids lacking DGK inhibitor in the presence of wild-type *L. reuteri* PTA-6475 conditioned media did not yield evidence of increased PKC phosphorylation, see FIGS. 5a and 5b.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

Thomas, et al. (2012). Histamine derived from probiotic *Lactobacillus reuteri* suppresses TNF via modulation of PKA and ERK signaling. PLoS One 7(2): e31951.

van Pijkeren and Britton. (2012). High efficiency recombineering in lactic acid bacteria. Nucleic Acids Research 40(10): e76.

Lee, et al. (2004). Dietary intake of various lactic acid bacteria suppresses type 2 helper T cell production in antigen-primed mice splenocyte. J. Microbiol. Biotechnol. 14(1): 167-170.

The invention claimed is:

1. A method of treating or reducing the risk of developing an allergy in a mammal, comprising
administering to a mammal in need thereof a diacylglycerol kinase (DagK) producing lactic acid bacterial strain that is capable of releasing DagK extracellularly, wherein the DagK producing lactic acid bacterial strain is not *L. reuteri* strain ATCC PTA-6475, *L. fermentum*, or *L. paracasei*.

2. The method of claim 1, wherein the allergy is a pollen allergy.

3. The method of claim 1, wherein the lactic acid bacterial strain is a *Lactobacillus reuteri*.

4. The method of claim 1, wherein the lactic acid bacterial strain is *L. reuteri* strain DSM 32273.

5. The method of claim 1, wherein the lactic acid bacterial strain is *L. reuteri* strain ATCC PTA-4659.

6. The method of claim 1, further comprising administering an H1-antihistamine.

7. The method of claim 6, wherein the H1 antihistamine is selected from a group consisting of cetirizine, ebastine, fexofenadine, loratadine and desloratadine.

\* \* \* \* \*

UNITED STATES PATENT AND TRADEMARK OFFICE
CERTIFICATE OF CORRECTION

PATENT NO. : 12,201,656 B2
APPLICATION NO. : 17/462227
DATED : January 21, 2025
INVENTOR(S) : Versalovic et al.

Page 1 of 2

It is certified that error appears in the above-identified patent and that said Letters Patent is hereby corrected as shown below:

In the Specification

Column 6, Lines 4-5: Please remove the paragraph break between "DagK." and "Corresponding"

Column 6, Line 40: Please correct "*L. cornposti,*" to read --*L. composti,*--

Column 6, Lines 42-43: Please correct "*L. delbrueckfi* subsp. *elbrueckii,*" to read --*L. delbrueckii* subsp. *elbrueckii,*--

Column 6, Line 43: Please correct "*L. delbrueckfi* subsp. *lactis,*" to read --*L. delbrueckii* subsp. *lactis,*--

Column 6, Line 44: Please correct "*L. aqui*" to read --*L. equi*--

Column 6, Line 45: Please correct "*L. fomicalis,*" to read --*L. fornicalis,*--

Column 6, Line 49: Please correct "*L. finers,*" to read --*L. iners,*--

Column 6, Line 52: Please correct "*L. mall,*" to read --*L. mali,*--

Column 11, Line 41: Please correct "other than 15 *L.*" to read --other than *L.*--

Column 11, Line 62: Please correct "Weg 1 b," to read --Weg 1b,--

Column 12, Line 35: Please correct "dagKmRNA" to read --dagK mRNA--

Column 12, Line 43: Please correct "LC-MSIMS" to read --LC-MS/MS--

Column 12, Line 55: Please correct "dagKtargeted" to read --dagK targeted--

Signed and Sealed this
Eighth Day of July, 2025

Coke Morgan Stewart
*Acting Director of the United States Patent and Trademark Office*

Column 12, Line 57: Please correct "IL-1a" to read --IL-1α--

Column 16, Line 4: Please correct "MSP, MSP," to read --M5P, M5P,--

SEQUENCE LISTING

```
<160> NUMBER OF SEQ ID NOS: 13

<210> SEQ ID NO 1
<211> LENGTH: 6
<212> TYPE: PRT
<213> ORGANISM: Lactobacillus reuteri

<400> SEQUENCE: 1

Glu Glu Arg Asn Met Arg
1               5

<210> SEQ ID NO 2
<211> LENGTH: 11
<212> TYPE: PRT
<213> ORGANISM: Lactobacillus reuteri

<400> SEQUENCE: 2

Asp Val Ala Ala Gly Gly Val Leu Ile Ser Ala
1               5                   10

<210> SEQ ID NO 3
<211> LENGTH: 7
<212> TYPE: PRT
<213> ORGANISM: Lactobacillus reuteri

<400> SEQUENCE: 3

Asp Lys His Gln Thr Glu Lys
1               5
```

```
<210> SEQ ID NO 4
<211> LENGTH: 13
<212> TYPE: PRT
<213> ORGANISM: Lactobacillus reuteri

<400> SEQUENCE: 4

Asn Met Arg Tyr His Leu Leu Ala Ala Cys Leu Ala Ile
1               5                   10

<210> SEQ ID NO 5
<211> LENGTH: 7
<212> TYPE: PRT
<213> ORGANISM: Lactobacillus reuteri

<400> SEQUENCE: 5

Glu Glu Arg Asn Met Arg Tyr
1               5

<210> SEQ ID NO 6
<211> LENGTH: 27
<212> TYPE: PRT
<213> ORGANISM: Lactobacillus reuteri

<400> SEQUENCE: 6

Lys Ala Lys Asp Val Ala Ala Gly Gly Val Leu Ile Ser Ala Ile Phe
1               5                   10                  15

Ser Val Leu Val Gly Leu Ile Ile Phe Ile Pro
            20                  25

<210> SEQ ID NO 7
<211> LENGTH: 8
<212> TYPE: PRT
<213> ORGANISM: Lactobacillus reuteri

<400> SEQUENCE: 7

Asp Val Ala Ala Gly Gly Val Leu
1               5

<210> SEQ ID NO 8
<211> LENGTH: 39
<212> TYPE: PRT
<213> ORGANISM: Lactobacillus reuteri

<400> SEQUENCE: 8

Asn Met Arg Tyr His Leu Leu Ala Ala Cys Leu Ala Ile Ile Met Ser
1               5                   10                  15

Ile Leu Leu His Ile Ser Ala Met Glu Trp Leu Trp Ile Leu Leu Ala
            20                  25                  30

Ile Phe Val Val Phe Thr Ser
        35

<210> SEQ ID NO 9
<211> LENGTH: 20
<212> TYPE: DNA
<213> ORGANISM: Artificial Sequence
<220> FEATURE:
<223> OTHER INFORMATION: Forward qRT - PCR primer for dagk gene

<400> SEQUENCE: 9
gcgtgagtcc ataaccgtct                                                20

<210> SEQ ID NO 10
<211> LENGTH: 20
<212> TYPE: DNA
```

```
<213> ORGANISM: Artificial Sequence
<220> FEATURE:
<223> OTHER INFORMATION: Reverse CRT - PCR primer for dagk gene

<400> SEQUENCE: 10
atggctgctg aaattcctgt                                                    20

<210> SEQ ID NO 11
<211> LENGTH: 22
<212> TYPE: DNA
<213> ORGANISM: Artificial Sequence
<220> FEATURE:
<223> OTHER INFORMATION: Forward PCR primer for dagk gene

<400> SEQUENCE: 11
tggactcacg cgataaacat ca                                                 22

<210> SEQ ID NO 12
<211> LENGTH: 24
<212> TYPE: DNA
<213> ORGANISM: Artificial Sequence
<220> FEATURE:
<223> OTHER INFORMATION: Reverse PCR primer for dagk gene

<400> SEQUENCE: 12
acaatcaaat ctgtaacagc ttcg                                               24

<210> SEQ ID NO 13
<211> LENGTH: 131
<212> TYPE: PRT
<213> ORGANISM: Lactobacillus reuteri

<400> SEQUENCE: 13

Met Asp Ser Arg Asp Lys His Gln Thr Glu Lys Asn His His Leu Ile
1               5                   10                  15

Gln Ala Met Arg His Ala Ile Asp Gly Ile Ile Gln Val Leu Arg Glu
            20                  25                  30

Glu Arg Asn Met Arg Tyr His Leu Leu Ala Ala Cys Leu Ala Ile Ile
        35                  40                  45

Met Ser Ala Leu Leu Gln Ile Ser Ala Met Glu Trp Leu Trp Ile Leu
    50                  55                  60

Leu Ala Ile Phe Val Val Phe Thr Ser Glu Phe Leu Asn Thr Val Thr
65                  70                  75                  80

Glu Ala Val Thr Asp Leu Ile Val Asp His His Tyr Glu Leu Asn Val
                85                  90                  95

Lys Lys Ala Lys Asp Val Ala Ala Gly Val Leu Ile Ser Ala Ile
            100                 105                 110

Phe Ser Val Leu Val Gly Leu Ile Ile Phe Ile Pro Arg Ile Leu Ala
            115                 120                 125

Ile Ile Arg
    130
```